United States Patent [19]

Bennewitz et al.

[11] 4,288,775
[45] Sep. 8, 1981

[54] DEVICE AND METHOD OF MANUFACTURING A RELATIVE HUMIDITY SENSOR AND TEMPERATURE SENSOR

[76] Inventors: Paul F. Bennewitz; Matt C. Bennewitz, both of 623 Wyoming, S.E., Albuquerque, N. Mex. 87123

[21] Appl. No.: 92,766

[22] Filed: Nov. 9, 1979

[51] Int. Cl.³ .............................................. H01L 7/00
[52] U.S. Cl. ...................................... 338/35; 338/25; 338/327; 338/328
[58] Field of Search ...................... 338/35, 13, 25, 34, 338/327, 328; 73/27; 324/61 R, 65 R; 422/98, 83, 88, ; 23/232 E; 340/602

[56] References Cited

U.S. PATENT DOCUMENTS

| | | | |
|---|---|---|---|
| 3,440,372 | 4/1969 | Cecil | 338/35 X |
| 3,523,244 | 8/1970 | Goodman et al. | 338/35 X |
| 3,550,057 | 12/1970 | Young | 338/35 X |
| 3,861,031 | 1/1975 | Furuichi | 338/35 X |
| 3,987,676 | 10/1976 | Bennewitz | 338/35 X |
| 4,143,177 | 3/1979 | Kovac et al. | 324/61 R X |
| 4,203,087 | 5/1980 | Kovac et al. | 73/336.5 X |

*Primary Examiner*—C. L. Albritton

*Attorney, Agent, or Firm*—William W. Cochran, II

[57] ABSTRACT

Sensor and method of fabricating a sensor for detecting relative humidity with a substantially linear response from 0% to 100% and also detecting temperature. The sensor utilizes a unique essentially pure $Al_2O_3$ layer which has a disordered crystalline structure and a density gradient which varies from a low density at its lower surface to a higher density at its upper surface which together produce the desired linear response to relative humidity. The method of producing the unique essentially pure $Al_2O_3$ layer includes anodizing with an ac current in a solution of approximately 6.4 normal acid at a starting temperature of 21° C. and allowing the temperature of the anodizing solution to rise with the process to vary the density of the $Al_2O_3$ layer. The $Al_2O_3$ layer is neutralized in a base solution, washed in boiling water and alcohol to neutralize the $Al_2O_3$ layer and remove impurities.

The sensor is employed as a three-terminal semiconducting device which is biased with dc current, allowing implementation with standard ICs and LSI circuitry. Application of a biasing current on the top electrode allows the RH sensor to be operated simultaneously as a temperature sensor.

6 Claims, 15 Drawing Figures

DEVICE AND METHOD OF MANUFACTURING A RELATIVE HUMIDITY SENSOR AND TEMPERATURE SENSOR

BACKGROUND OF THE INVENTION

The present invention pertains generally to Humidity Sensors and more particularly to sensors and methods of fabricating sensors for detecting relative humidity and temperature.

Conventional humidity sensors utilize an aluminum layer which is partially anodized on its upper surface prior to deposition of the top electrode. The upper electrode is sufficiently thin to allow passage of water molecules to the $Al_2O_3$ layer which changes resistance and capacitance when employed in a conventional ac stabilization circuit.

Although conventional humidity sensors have been developed to provide good response, slow anodization of the aluminum base material causes progressive impedance and capacitance change in the sensor due to exposure to moisture and residual acid remaining in the $Al_2O_3$ layer after the initial anodization process, especially when subjected to an ac current as utilized in conventional humidity sensor circuitry. As a result, the humidity detecting circuitry must be continually adjusted for proper operation throughout the life of the device. Even more seriously, use of the device in high temperature environments causes rapid aging even though appreciable amounts of moisture may not be present.

Attempts to overcome these problems by methods such as pre-aging the sensor, as disclosed in the prior art, have had limited success due to the non-transient nature of the slow anodization process.

Another attempt to overcome these problems is disclosed in U.S. Pat. No. 4,143,177 issued Mar. 6, 1979 to Kovac et al wherein a substantial portion of the Al metal present in the Al layer is removed by anodizing the Al layer using conventional anodization methods. As set forth, this process is used in an attempt to provide high temperature stability of the absolute humidity sensor disclosed by Kovac et al since a major portion of the Al metal left in the sensor which can become oxidized during operation or storage of high temperatures, is removed, which would otherwise affect the sensitivity and, consequently, calibration of the sensor.

However, since the $Al_2O_3$ layer of the Kovac et al sensor is formed according to conventional anodizing methods, the Kovac et al humidity detector is incapable of providing a linear response with respect to relative humidity. Rather, the Kovac et al detector can only provide a non-linear response to absolute humidity due to the structure and density of the $Al_2O_3$ layer resulting from the manner in which the $Al_2O_3$ is produced, i.e., with conventional anodizing methods. Furthermore, conventional methods of anodizing utilized by Kovac et al cannot remove essentially all the Al metal and other impurities in the $Al_2O_3$ layer, but only a substantial portion, as set forth in U.S. Pat. No. 4,143,177.

SUMMARY OF THE INVENTION

The present invention overcomes the disadvantages and limitations of the prior art by providing an improved relative humidity sensor and a method of producing the same which can also be used simultaneously as a temperature sensor. This is accomplished by anodizing a layer of Al metal in freshly mixed acid at a starting temperature of approximately 21° C. and allowing the temperature of the acid to rise during the process so that the density of the $Al_2O_3$ layer is less at lower levels of the $Al_2O_3$ layer. This process also prevents the formation of pores which penetrate the entire thickness of the anodized layer, such as produced in conventional anodizing processes. Rather, the process of anodizing according to the present invention produces a disordered crystalline structure of $Al_2O_3$ having a density gradient which results in a substantially linear respose of the sensor to relative humidities ranging between 0% and 100%. Residual acid remaining in the anodized layer is then neutralized in a base solution which also functions to remove essentially all residues of Al metal and other impurities in the anodized layer. The resulting essentially pure layer of $Al_2O_3$ provides a stable semiconductor which does not exhibit progressive impedance or capacitive changes due to corrosion or other manifestations of aging.

The sensor, using the essentially pure $Al_2O_3$ layer, can be employed as a 3-terminal semiconductor device which can be biased with low level dc currents thereby enhancing direct implementation of the sensor with ICs (integrated circuits) and LSIs (large-scale integrated circuits). The sensor can additionally be employed to detect temperature by proper biasing of the upper electrode which displays a linear variation of resistance with changes in temperature.

OBJECTS OF THE INVENTION

It is therefore an object of the present invention to provide an improved relative humidity sensor and method of fibrication of the same.

It is also an object of the present invention to provide a relative humidity sensor and method of fabricating the same which is not subject to progressive aging or corrosion.

Another object of the present invention is to provide a relative humidity sensor and method of fabricating the same which produces a linear response to relative humidity ranging between 0% and 100%.

Another object of the present invention is to provide a relative humidity sensor which can be operated as a three-terminal device utilizing a direct current biasing source.

Another object of the present invention is to provide a method of producing a layer of essentially pure $Al_2O_3$ for use as a semiconductor material.

Another object of the present invention is to provide a microminiature sensor which can be directly incorporated in ICs and LSI circuitry.

Another object of the present invention is to provide a sensor capable of detecting both temperature and percent of relative humidity, simultaneously.

Another object of the present invention is to provide a relative humidity sensor which can be operated in high temperature environments without aging.

Other objects, advantages and novel features of the present invention will become apparent from the following detailed description of the invention when considered in conjunction with the accompanying drawings wherein:

BRIEF DESCRIPTION OF THE DRAWINGS

FIG. 3b is a top view of the bottom electrode deposited on the device of FIG. 3a.

DETAILED DESCRIPTION OF THE PREFERRED EMBODIMENT OF THE INVENTION

Figure 1:
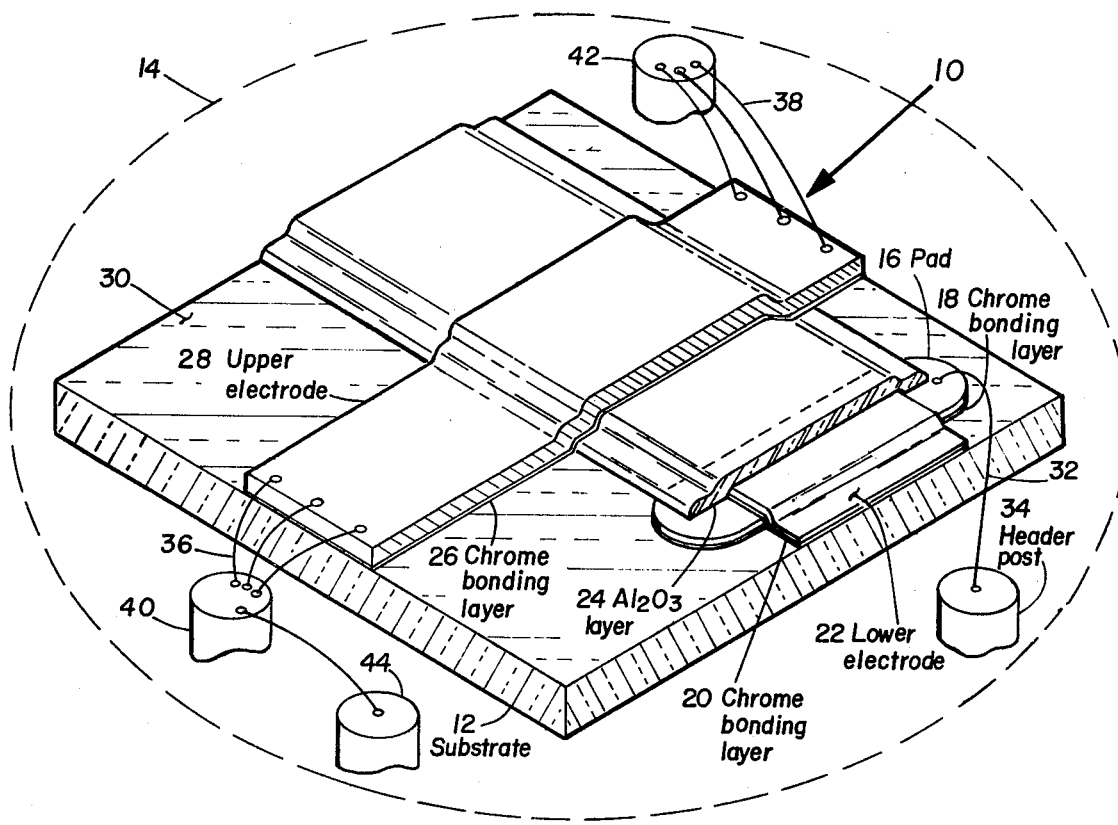
FIG. 1 is a perspective view of the sensor of the present invention.

FIG. 1 illustrates the sensor of the preferred embodiment of the present invention for detecting percentage, in the surrounding environment, of relative humidity. The device can also be used to simultaneously detect temperature utilizing the various circuitry disclosed herein.

Relative humidity sensors have a variety of utilities. For example, relative humidity sensors have been used for environmental control in grain silos, human habitat, computer rooms and military and commercial aircraft. They have also been used in automotive and aircraft systems for carburation control, rust studies, passenger environmental control, engine test cell monitoring, and to detect icing conditions on aircraft, highways, radar antennae, television broadcast antennae, turbines, etc. The sensors have also been used for moisture and leak detection in the NASA Space Shuttle engine, aircraft cooling systems, fuel tanks, sonar buoys, ammunition depot storage, torpedoes, waveguide transmission lines, hybrid circuits to test hermeticity, silo missile storage, heart pacemakers, gas-cooled reactors, and nuclear weapons. The sensors have additionally been used in humidity and temperature calibration systems in meteorology labs, sterilizers, film developing and calibration of radiosonde and dropsonde.

Referring again to FIG. 1, the sensor comprises a substrate 12 which is formed of quartz, amorphous glass or similar material. The particular choice of substrate material is not critical, but should be a material which is electrically insulating, and which has a relatively low temperature coefficient approximating that of subsequent layers to be deposited thereon, as described below. It has been found that amorphous quartz is particularly well suited for such use. A quartz substrate has been used in the present invention which measures 0.075"×0.070"×0.010", mounted on a standard header 14.

Deposited on substrate 12 is pad 16 formed from five nines pure gold or other noble metal having a thickness of approximately 10,000 Å, which overlies a chrome bonding layer 18 having a thickness of approximately 140 Å. Deposited over pad 16 is a chrome bonding layer 20 similar to chrome bonding layer 18. Lower electrode 22 is then deposited over chrome bonding layer 20. Lower electrode 22 is formed of five nines pure gold or other noble metal which is not affected by treatments in acid or base solutions.

Overlying the lower electrode 22 is a layer of essentially pure $Al_2O_3$ 24 which is substantially transparent, formed from a layer of Al metal having a thickness of appproximately 120 Å to 5000 Å, according the method of the preferred embodiment of the invention. As shown in FIG. 1, the $Al_2O_3$ layer extends beyond the edges of lower electrode 22 by approximately 2 to 4 mils to ensure electrical insulation of the lower electrode 22 from subsequently deposited layers. Chrome bonding layer 26 is deposited across the composite layers described above, such that layer 26 is deposited directly on the upper surface 30 of substrate 12 and upper surface of $Al_2O_3$ layer 24. Directly over chrome bonding layer 26 is deposited an upper electrode 28 of five nines pure gold or other suitable electrode material such as nickel, indium, or a noble metal, etc., depending upon the intended utilization of the electrode. The upper electrode 28, which is also referred to as the control electrode, has a thickness for gold ranging from approximately 7 Å to 1000 Å, limited in thinness by the conductivity of the metal and its ability to carry the requisite biasing currents, and in thickness by the porosity of the metal and its ability to pass water molecules to $Al_2O_3$ layer 24. The thickness for other metals such as nickel, indium, platinum, etc., of course, varies according to the characteristics of the metal and its ability to meet the above criteria. Since the upper electrode can also be used as a temperature sensor, which, when properly biased, exhibits a positive temperature coefficient in dc resistance, the thickness of the upper electrode and biasing current employed are design parameters which affect performance of the sensor depending upon its intended application.

Electrical connection to the lower electrode 22 is accomplished by attaching wire 32 between pad 16 and header post 34. To provide uniform distribution of biasing current, to spread the dc field through the $Al_2O_3$ lyaer 24 from the upper electrode 28, and to ensure that sufficient current can be carried, the plurality of wires 36 and 38 are attached evenly along the ends of upper electrode 28 to header posts 40 and 42, respectively. Each of the wires has a diameter of approximately 1-2 mils. Header post 44 is connected to header post 40 to act as a ground terminal or system common. Header post 42 is connected to the bias voltage while header post 34 functions as a signal terminal.

Figure 2:
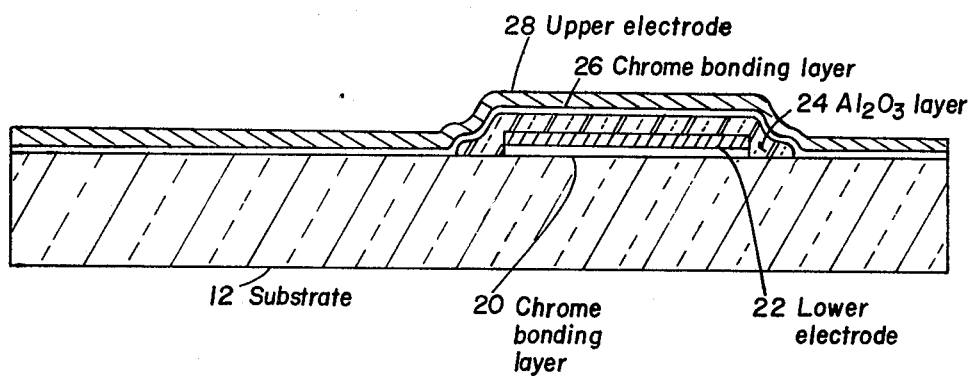
FIG. 2 is a cross-section of the sensor as shown in FIG. 3e.
Figure 3A:
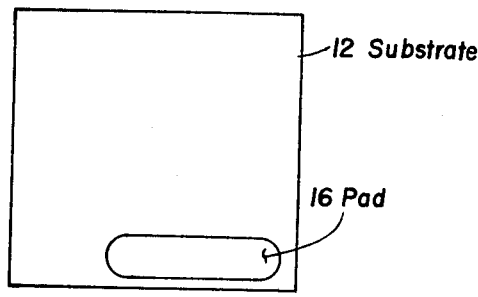
FIG. 3a is a top view of the substrate with a pad deposited thereon.
Figure 3B:
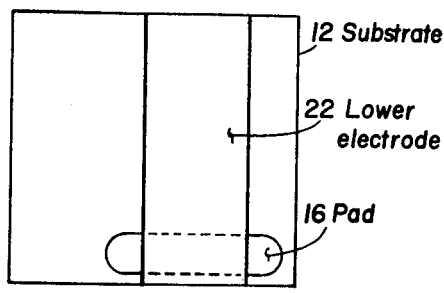
Figure 3C:
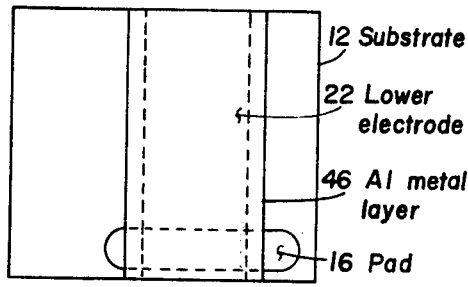
FIG. 3c is a top view of the Al metal layer deposited on the device of FIG. 3b.
Figure 3D:
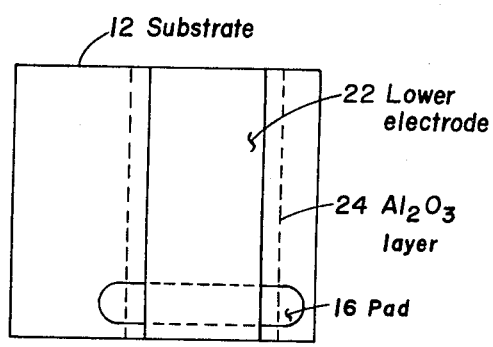
FIG. 3d is a top view of the device of FIG. 3c after the Al metal layer is anodized to form a layer of essentially pure $Al_2O_3$.
Figure 3E:
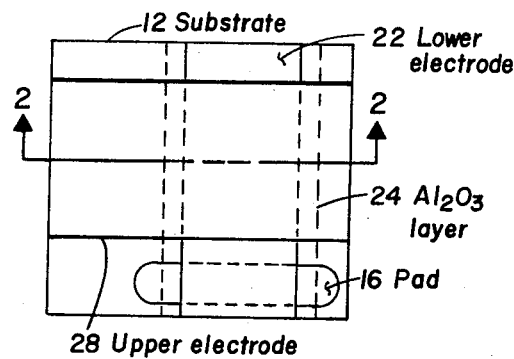
FIG. 3e is a top view of the final configuration showing the upper gold electrode deposited on the device of FIG. 3d.

FIG. 2 is a cross-sectional diagram of the sensor taken as shown in FIG. 3e. As in FIG. 1, the layers are shown schematically and are not drawn to scale. FIG. 2 illustrates the relationship of the various layers and substrate 12 to one another.

FIGS. 3a–3e illustrate the method of fabrication of the sensor of the present invention.

FIG. 3a is a top view of the substrate with pad 16 and chrome bonding layer 18 deposited thereon. The substrate 12 is freshly cleaved or sputtered prior to the deposition of the chrome bonding layer 18 to ensure bonding. The chrome layer 18 functions as a bonding layer for pad 16 on substrate 12. The chrome layer 18 is deposited to a thickness of approximately 140 Å while pad 16 is deposited directly over chrome bonding layer 18, without breaking vacuum, to a thickness of approximately 10,000 Å. The composite of FIG. 3a is then sputter cleaned for approximately two minutes to remove residual gas and impurities.

FIG. 3b illustrates the deposition of the lower electrode 22 formed from five nines pure gold, or other noble metal such as platinum, over the substrate 12 and upper surface of pad 16. Appropriate masking is used to deposit both chrome bonding layer 20 and lower electrode 22 without breaking vacuum. Again, the substrate should be freshly sputtered or cleaved to ensure bonding. The chrome layer 20 is approximatey 140 Å thick while the lower electrode 22 is approximately 400 Å to 3000 Å thick.

The composite of FIG. 3 is then sputtered in a vacuum for approximately five minutes to roughen the pre-applied layers and to remove a number of angstroms from both the substrate 12 and layer interfaces, so as to provide a freshly cleaved surface to promote good adhesion of the finished semiconducting $Al_2O_3$ layer 24.

The composite is then masked for deposition of a layer 46 of five nines pure Al metal as shown in FIG. 3c. The Al metal layer 46 has a thickness ranging from 120 Å to 5000 Å depending upon final desired device characteristics. The Al metal layer 46 overlaps the lower electrode 22 by approximately 2–4 mils. The composite of FIG. 3c is then anodized in a particular manner in a special anodizing solution, as set forth below, to produce the novel and unique layer of essentially pure $Al_2O_3$ 24.

The anodizing solution is prepared in an optically clear container for visual observation purposes. The solution is prepared by mixing 17% by volume of 98% pure sulfuric acid with HPLC (purified) water. The solution prepared as set forth above, has a normality of approximately 6.4 gram equivalent weights/liter. While the solution is prepared in a particular manner as set forth above with sulfuric acid, other suitable methods of preparing the solution and even use of other suitable acids to obtain a freshly mixed solution having a normality of approximately 6.4 gram equivalent weights/liter, are acceptable.

The freshly mixed solution is then placed in a refrigeration unit and cooled to 18° C. Once cooled to 18° C., the solution is removed from the refrigeration unit and allowed to warm to approximately 21° C. in room temperature environment. The temperature of the solution rises naturally due to the continuing reaction taking place in the solution. It is important to note that some reaction must be taking place in the solution to obtain the desired results from the anodizing process.

The substrate is then connected to one side of a 60 Hz ac electrical signal while the other side is connected to a five nines pure aluminum electrode (anode). Once the solution reaches 21° C., the anode and substrate are placed in the solution with the deposited layers facing away from the anode. The voltage is carefully controlled to produce a 0.5 volt ac drop across a 10 ohm precision resistor placed in series with the anode.

The process is then viewed with a medium power stereo zoom microscope. The solution is not temperature controlled but the anodizing process should be performed in a room environment of approximately 20° C. Once the anodizing process starts, the solution will increase in temperature at a predetermined rate determined by the anodization process. The solution will normally increase 4–7° C. during the process which causes the layer of $Al_2O_3$ to have a density gradient which varies throughout the thickness of the $Al_2O_3$ layer from more dense on its upper surface to less dense at its lower surface. This density gradient is necessary to produce a substantially linear response to changes in relative humidity from 0% to 100% RH.

When viewing the anodization process through the microscope, bubbles of gas are seen forming on the Al metal and releasing to go to the surface. The anodization process increases as the solution increases in temperature evidenced by rapidly accelerated bubbling. When bubbling is observed to decrease at a rapid rate and the lower electrode 22 becomes visible through the anodized layer, the composite is rapidly removed and disconnected from the ac electrical source and placed in HPLC water. The anodized layer should then be gently rinsed in HPLC water for 5 to 15 seconds.

Following a second rinse in HPLC water, the composite is placed, without drying, into a 10% solution of ammonium hydroxide for approximately 10 seconds. The ammonium hydroxide solution neutralizes and removes all traces of acid, residues of aluminum, and other impurities in the layer of $Al_2O_3$ 24 formed from the Al metal layer 46. Of course, other equivalent mixtures and/or bases can be used for the neutralization process as set forth above.

The $Al_2O_3$ layer 24 should then be rinsed thoroughly again in HPLC water, dipped into a clean rinse of HPLC water and plunged into a boiling solution of HPLC water for approximately 2 minutes. The composite should then be dipped into $CH_3CH(OH)CH_3$ to remove excess $H_2O$, followed by two separate dips in fresh $CH_3CH(OH)CH_3$. The composite is then dried in a filtered stream of nitrogen.

Upon observation of the composite, no $Al_2O_3$ layer is visible with the naked eye or under a low-power microscope. However, under higher power, the substantially transparent layer of $Al_2O_3$ 24 is visible. This is more clearly shown in FIG. 3d where $Al_2O_3$ layer 24 is essentially transparent such that the lower electrode 22 is clearly visible. By following the above process, the essentially pure layer of $Al_2O_3$ is approximately the same thickness as the original Al metal layer 46.

The composite of FIG. 3d is then placed in a clean, covered, petri dish and placed in a dry oven at 105° C. for 24 hours. This step anneals the $Al_2O_3$ layer to the lower electrode 22 and substrate 12 to prevent crazing, cracking and pealing during final processing.

Following the annealing process, the composite is placed immediately in a vacuum for deposition of additional layers of the sensor 10. Pump-down should be instituted as soon as possible and continued until $10^{-6}$ torr is obtained. A chrome bonding layer 26 is then deposited to a thickness of approximately 140 Å, followed by deposition of the upper electrode 28 to a total thickness of approximately 400 Å including the chrome layer 26, in a configuration as shown in FIG. 3e and FIG. 1.

Following pump-down, the sensor illustrated in FIG. 3e is placed in a covered petri dish and placed in a dry oven at 125° C. for 72 hours. Heating treating, in this manner, anneals the composite sensor to prevent pealing, crazing, cracking, etc., as set forth above. The sensor may then be left at ambient temperature until divided into individual sensors.

Although FIGS. 3a-3e illustrate the above process as fabrication of a single sensor, in actuality a number of sensors are fabricated simultaneously by depositing long strips of the various layers in a patchwork pattern on a longer substrate. The larger substrate is then divided into a plurality of smaller, single sensors illustrated in FIGS. 1 and 3e.

The invididual sensors are then mounted on the desired header and electrically connected to header posts and packaged in the desired manner for the intended use. Of course, the sensor can be packaged directly with the processing integrated circuitry due to its size and ability to be operated with dc biasing.

Auger analysis of the $Al_2O_3$ layer formed according to the disclosed method reveals no detectable Al metal present. Microscopic inspection of the essentially pure $Al_2O_3$ layer reveals a disordered crystalline structure with very short pores penetrating the upper surface, or no pores at all. The upper region of the $Al_2O_3$ layer, which was anodized in a cooler acid solution, is denser than lower regions which were anodized in a higher temperature acid solution at a more rapid rate. The density of the essentially pure $Al_2O_3$ layer consequently forms a density gradient which increases progressively from the upper surface to the lower surface. This provides a linear response of the sensor for the complete range of relative humidities from 0% to 100% RH. The neutralization of acid and removal of impurities using the base solution additionally ensures that the sensor will not be subject to progressive aging.

Figure 4:
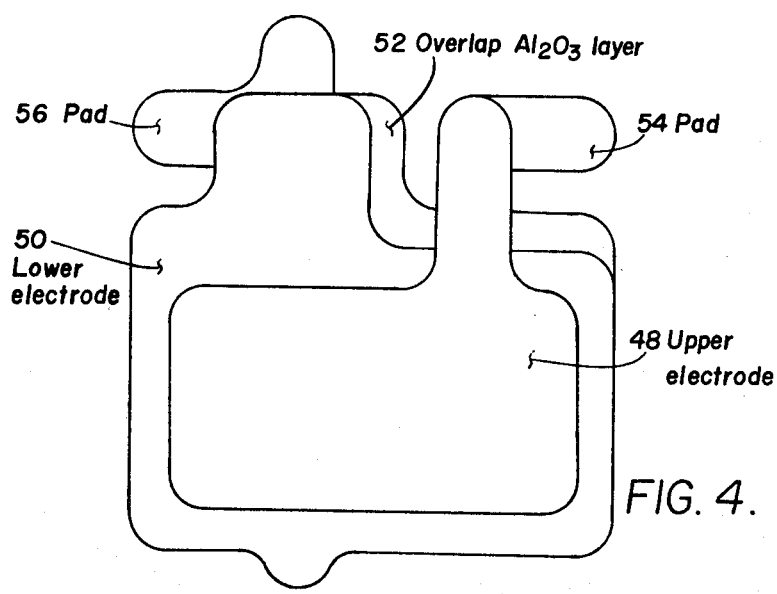
FIG. 4 is an alternative sensor configuration.

FIG. 4 illustrates an alternative arrangement of layers to produce a sensor in accordance with the preferred embodiment of the invention. The sensor portion comprises an upper electrode 48, lower electrode 50, and an $Al_2O_3$ layer 52. Pads 54 and 56 function as electrical connectors to the electrodes. Additionally, electrical wires can be connected directly to upper electrode 48.

Figure 5:
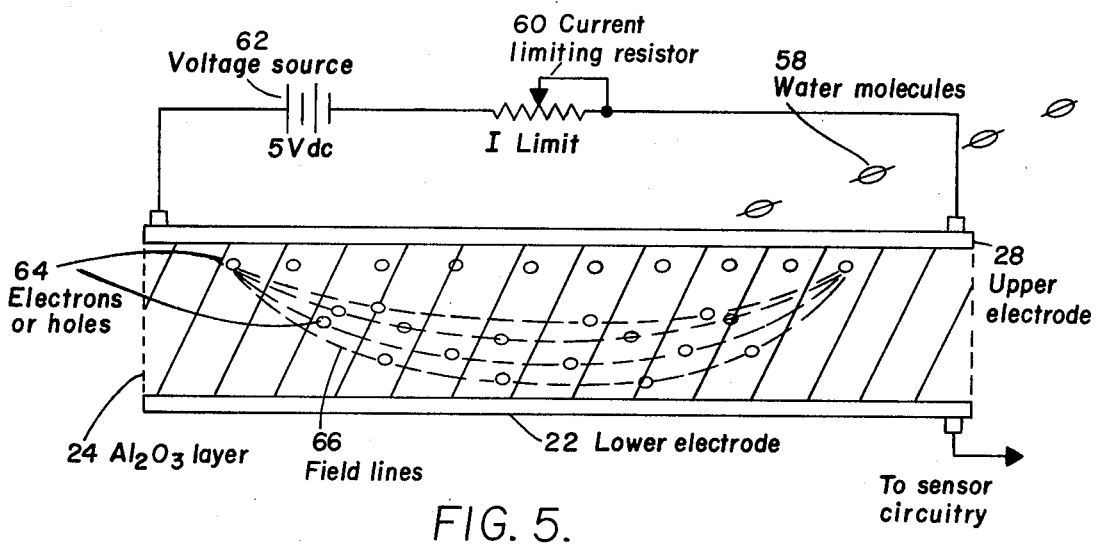
FIG. 5 is a schematic diagram of a biased sensor illustrating the effect of biasing.

FIG. 5 is a schematic diagram illustrating the manner in which the sensor 10 of the present invention may be used as a three terminal device. As opposed to prior art sensors which are used as capacitors in conjunction with an alternating current signal to detect changes in humidity, the present invention uses a dc bias signal provided by voltage source 62 and current limiting resistor 60 to operate the sensor as a semiconductor device. The bias provided on the control electrode or upper electrode 28, as shown in FIG. 5, generates a fixed field in the $Al_2O_3$ semiconducting layer 24 shown by field lines 66. The field lines prevent the movement of dipoles (water molecules) through $Al_2O_3$ layer 24 at different energy levels. Energy from water molecules 58 which have an energy level determined by their temperature, penetrate the upper electrode 28 and $Al_2O_3$ layer 24 causing the $Al_2O_3$ layer to conduct more or less depending upon the density of water molecules 58 and their thermal energy.

Figure 6:
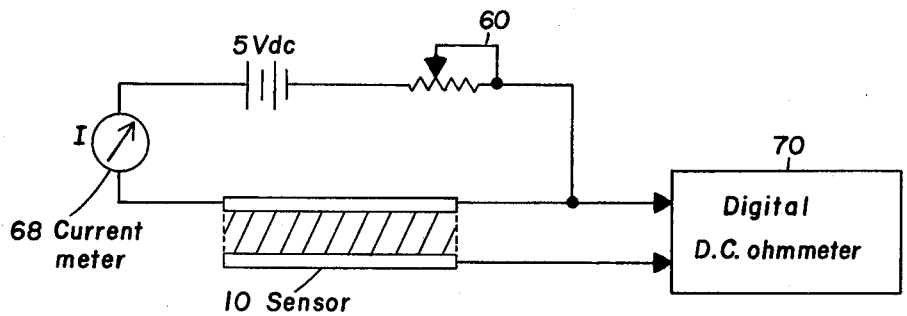
FIG. 6 is a test circuit for measuring series dc resistance change of the $Al_2O_3$ layer with changing bias control current.
Figure 7:
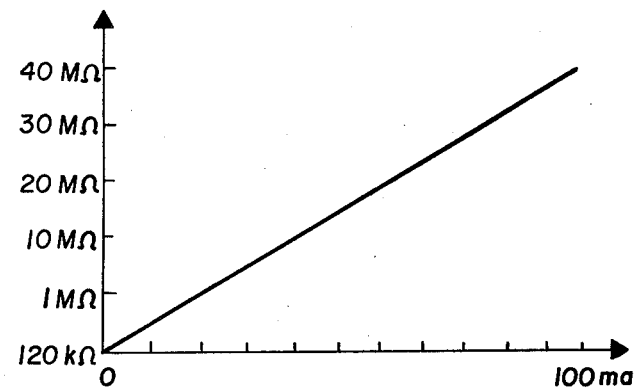
FIG. 7 is a graph of resistance in ohms vs. current in milliamps illustrating the series dc resistance change of the $Al_2O_3$ layer with changing bias control current, as measured by the device of FIG. 6.

FIGS. 6 and 7 illustrate the series dc resistance measured between the upper electrode 28 and lower electrode 22 for various currents applied to upper electrode 28. A gating or blocking effect is produced in the sensor 10 that causes the series dc resistance measured by ohmmeter 70 to vary linearly with the amount of biasing current applied, as measured by current meter 68 and controlled by current limiting resistor 60.

A typical response for a detector produced in accordance with the present invention is graphically illustrated in FIG. 7. As shown, currents of a few milliamps will cause the series dc resistance of the sensor to increase by several megaohms. Currents of 100 ma to 200 ma produce heating in the device and increase the series dc resistance several orders of magnitude. As shown in FIG. 7, currents as low as 1 ma are sufficient to bias the sensor for operation as a three-terminal device which provides a linear response to changes in relative humidity.

In the course of development of the present invention, dc ohmic measurements were made across the length of upper electrode 28 which was found to display a resistance, end to end, of approximately 4.5 ohms to 5.5 ohms or slightly higher. It was also found that the upper electrode 28 displays a positive linear resistance coefficient with changes in temperature of the sensor which is not affected by changes in humidity. Sensor 10 can therefore be operated as a temperature sensor and a relative humidity sensor simultaneously.

Figure 8:
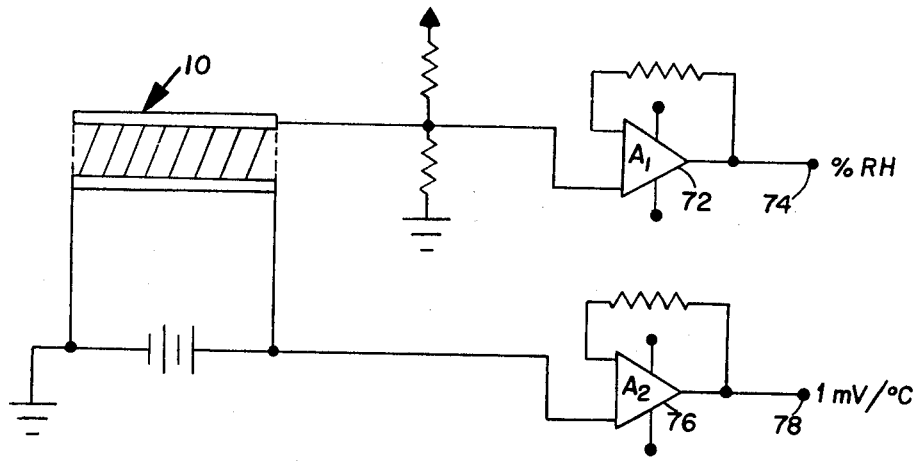
FIG. 8 is a schematic diagram of a circuit arrangement for measuring both percentage of relative humidity and temperature from a single sensor.
Figure 9:
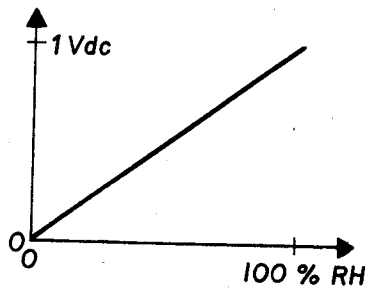
FIG. 9 is a graph illustrating results of detected percentage of relative humidity from the circuit of FIG. 8.

FIG. 8 is a schematic diagram of a typical circuit for operating sensor 10 as both a temperature sensor and relative humidity sensor. Amplifier ($A_1$) 72 is adjusted to produce 1 millivolt/% RH at output 74 so that 1 volt dc is equivalent to 100% RH. A typical linear response of sensor 10 produced at output 74 is illustrated in FIG. 9.

Figure 10:
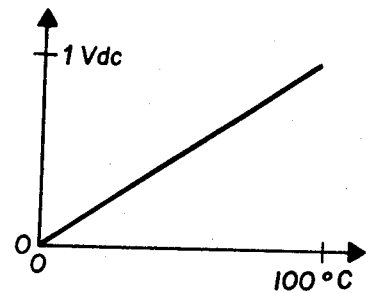
FIG. 10 is a graph illustrating results of detected temperature from the circuit of FIG. 8.

Amplifier ($A_2$) 76 is adjusted to produce 1 millivolt/°C. so that output 78 produces outputs which vary between zero volts dc and 1 volt dc, representing changes from 0° C. to 100° C., as shown in FIG. 10.

Figure 11:
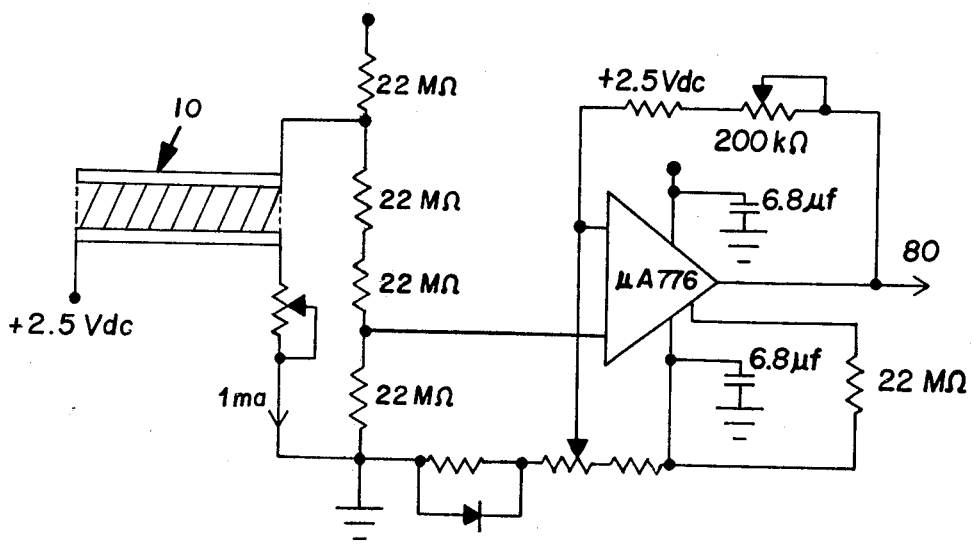
FIG. 11 is a schematic diagram of a particular low current dc amplification circuit.

A particular amplification configuration to detect relative humidity is schematically illustrated in FIG. 11. With proper biasing of the sensor, the voltage at output 80 varies between 0-1 V dc to indicate changes in humidity of 0%-100% RH.

The present invention therefore provides a sensor and method of fabrication of a sensor which is capable of detecting changes in RH in a linear manner between 0% to 100% RH. The linear response of the sensor 10 is a result of the disordered crystalline structure of the essentially pure $Al_2O_3$ layer which has a density gradient which varies from denser to less dense from its upper surface to its lower surface. The particular method of fabrication, i.e., utilizing a particular starting temperature, e.g., 21° C., and allowing the temperature to rise at its own rate during the anodization process, gives rise to the disordered crystalline structure and density gradient which allows the sensor 10 to operate in a linear manner in response to changes in RH. Neutralization and removal of impurities from essentially pure $Al_2O_3$ layer also prevents progressive periodic recalibration resulting from progressive aging.

Furthermore, sensor 10 is employed as a three-terminal semiconductor device which is biased with direct current allowing the sensor to be incorporated direcly with integrated circuits (ICs) and large-scale integrated circuits (LSIs). This greatly reduces costs and allows packaging of the entire device in microminiature circuitry packages so as to greatly increase the utility of the device due to its decreased size and reduced power requirements.

The sensor can also simultaneously function as a temperature sensor further increasing its utility for application where both relative humidity and temperature are desired. Among other applications, this is particularly useful for detecting icing conditions.

Consequently, the sensor of the present invention comprises a novel and unique device having greatly increased utility and reliability over prior art sensors, due to both its method of fabrication and implementation.

Obviously, many modifications and variations of the present invention are possible in light of the above teachings. For example, the particular configuration of the sensor is not critical to its operation. Configurations other than those specifically shown in FIGS. 1 and 4 can be used in an equivalent manner. Moreover, the sensor can be used in any desired packaging arrangement, depending upon the intended use of the device. Also, if desired, temperature information can be fed back to RH processing circuitry to adjust RH sensor readings to eliminate the need for external thermistors, where applicable. It is therefore to be understood that within the scope of the appended claims, the invention may be practiced otherwise than as specifically described, and that subject matter disclosed herein shall not be precluded from being later claimed in the present application, or a continuation, continuation-in-part, or reissue application.

What is claimed is:

1. A semiconductor for use as a sensor for detecting relative humidity comprising:
   a lower electrode formed from a noble metal;
   an essentially pure layer of $Al_2O_3$ having a thickness ranging from approximately 120 angstroms to 5000 angstroms deposited on said lower electrode, said layer of $Al_2O_3$ having a disordered crystalline structure and a density gradient which varies progressively through the thickness of said layer of $Al_2O_3$ from a less dense structure at the lower surface of said layer of $Al_2O_3$ adjacent said lower electrode to a more dense structure at the upper surface of said layer of $Al_2O_3$;
   an upper electrode deposited on said upper surface of said layer of $Al_2O_3$, said upper electrode having a thickness ranging from approximately 7 Å to approximately 1000 Å;
   whereby said disordered crystalline structure and said density gradient of said layer of $Al_2O_3$ function to produce a linear response to relative humidity from said sensor.

2. The semiconductor of claim 1 further comprising:
   a substrate;
   a chrome layer deposited on said substrate between said substrate and said lower electrode;
   a chrome layer deposited between said layer of $Al_2O_3$ and said lower electrode and said substrate.

3. The semiconductor of claim 1 wherein said upper electrode is formed from a noble metal.

4. The semiconductor of claim 1 wherein said upper electrode is formed from nickel.

5. The semiconductor of claim 1 wherein said upper electrode is formed from indium.

6. A semiconductor for use as a sensor for detecting relative humidity and temperature simultaneously comprising:
   a lower electrode formed from a noble metal;
   an essentially pure layer of $Al_2O_3$ having a thickness ranging from approximately 120 angstroms to 5000 angstroms deposited on said lower electrode, said layer of $Al_2O_3$ having a disordered crystalline structure and a density gradient which varies progressively through the thickness of said layer of $Al_2O_3$ from a less dense structure at the lower surface of said layer of $Al_2O_3$ adjacent said lower electrode to a more dense structure at the upper surface of said layer of $Al_2O_3$;
   an upper electrode deposited on said upper surface of said layer of $Al_2O_3$, said upper electrode having a thickness ranging from approximately 7 Å to approximately 1000 Å;
   whereby said disordered crystalline structure and said density gradient of said layer of $Al_2O_3$ function to produce a linear response to relative humidity from said sensor and said upper electrode displays a change in resistance to changes in temperature when biased with a dc source.

* * * * *

UNITED STATES PATENT AND TRADEMARK OFFICE
CERTIFICATE OF CORRECTION

PATENT NO. : B1 4,288,775
DATED : September 8, 1982
INVENTOR(S) : Bennewitz et al.

It is certified that error appears in the above-identified patent and that said Letters Patent are hereby corrected as shown below:

Claim 1, line 25, column 1 should read --5,000 angstroms-- instead of "500 angstroms".

Signed and Sealed this

Second Day of October 1984

[SEAL]

Attest:

Attesting Officer

GERALD J. MOSSINGHOFF
Commissioner of Patents and Trademarks

REEXAMINATION CERTIFICATE (90th)

United States Patent [19]
Bennewitz et al.

[11] B1 4,288,775
[45] Certificate Issued May 31, 1983

[54] DEVICE AND METHOD OF MANUFACTURING A RELATIVE HUMIDITY SENSOR AND TEMPERATURE SENSOR

[76] Inventors: Paul F. Bennewitz; Matt C. Bennewitz, both of 623 Wyoming, SE. Albuquerque, N. Mex. 87123

Reexamination Request
No. 90/000,208, Jun. 1, 1982

Reexamination Certificate for:
Patent No.: 4,288,775
Issued: Sep. 8, 1981
Appl. No.: 92,766
Filed: Nov. 9, 1979

[51] Int. Cl.³ .......................................... H01L 7/00
[52] U.S. Cl. ........ 338/35; 338/25; 338/327; 338/328
[58] Field of Search ................. 338/35, 13, 25, 34, 327; 338/328; 73/27; 324/61 R; 65 R; 422/98, 83, 88; 23/252 E; 340/602

[56] References Cited

U.S. PATENT DOCUMENTS

| | | | |
|---|---|---|---|
| 1,415,748 | 5/1922 | Weintraub | 338/25 |
| 2,580,737 | 1/1952 | Davis | 252/408 |
| 3,067,310 | 12/1962 | Walz et al. | 338/308 |
| 3,075,385 | 1/1963 | Stover | 73/335 |
| 3,121,853 | 2/1964 | Jason et al. | 338/35 |
| 3,255,324 | 6/1966 | Ovshinsky | 338/324 |
| 3,343,075 | 9/1967 | Ovshinsky | 338/34 |
| 3,345,596 | 10/1967 | Delaney et al. | 338/35 |
| 3,440,372 | 4/1969 | Cecil | 338/35 |
| 3,523,244 | 8/1970 | Goodman | 338/35 |
| 3,539,917 | 10/1970 | Chleck | 324/61 |
| 3,540,278 | 11/1970 | Diamond et al. | 73/336.5 |
| 3,550,057 | 12/1970 | Young | 338/35 |
| 3,683,243 | 8/1972 | Rockliff | 361/286 |
| 3,703,697 | 11/1972 | Nicholas | 338/35 |
| 3,861,031 | 1/1975 | Furnichi | 338/35 |
| 3,987,676 | 10/1976 | Bennewitz | 338/35 |
| 4,080,564 | 3/1978 | Nitta et al. | 324/65 R |
| 4,143,177 | 3/1979 | Kovac et al. | 324/61 R |
| 4,203,087 | 5/1980 | Kovac et al. | 73/336.5 |

OTHER PUBLICATIONS

Choo & Devereux, "Barrier-Type Aluminum Oxide Films Formed Under Prolonged Anodizing, *J. Electrochemical Soc.* (Dec. 1975), p. 1645.

O'Sullivan & Wood, "The Morphology and Mechanism of Formation of Porous Anodic Films on Aluminum," Proc. Roy. Soc. Lond. (1970), p. 511.

*Primary Examiner*—C. L. Albritton

[57] ABSTRACT

Sensor and method of fabricating a sensor for detecting relative humidity with a substantially linear response from 0% to 100% and also detecting temperature. The sensor utilizes a unique essentially pure $Al_2O_3$ layer which has a disordered crystalline structure and a density gradient which varies from a low density at its lower surface to a higher density at its upper surface which together produce the desired linear response to relative humidity. The method of producing the unique essentially pure $Al_2O_3$ layer includes anodizing with an ac current in a solution of approximately 6.4 normal acid at a starting temperature of 21° C. and allowing the temperature of the anodizing solution to rise with the process to vary the density of the $Al_2O_3$ layer. The $Al_2O_3$ layer is neutralized in a base solution, washed in boiling water and alcohol to neutralize the $Al_2O_3$ layer and remove impurities.

The sensor is employed as a three-terminal semiconducting device which is biased with dc current, allowing implementation with standard ICs and LSI circuitry. Application of a biasing current on the top electrode allows the RH sensor to be operated simultaneously as a temperature sensor.

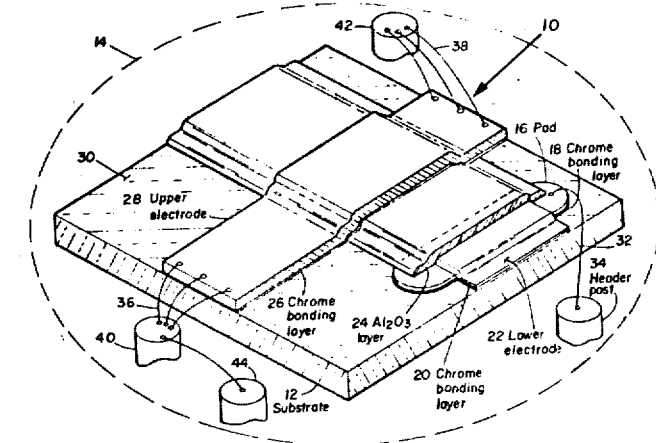

1

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 6 are determined to be patentable as amended:

1. A semiconductor for use as a sensor for detecting relative humidity *which does not exhibit progressive aging* comprising:
   a lower electrode formed from a noble metal;
   an essentially pure layer of $Al_2O_3$ having a thickness ranging from approximately 120 angstroms to 500 angstroms deposited on said lower electrode, said layer of $Al_2O_3$ having a disordered crystalline structure *without pores* and a density gradient which varies progressively through the thickness of said layer of $Al_2O_3$ from a less dense structure at the lower surface of said layer of $Al_2O_3$ adjacent said lower electrode to a more dense structure at the upper surface of said layer of $Al_2O_3$;
   an upper electrode deposited on said upper surface of said layer of $Al_2O_3$, said upper electrode having a thickness ranging from approximately 7 Å to approximately 1000 Å;
   whereby said disordered crystalline structure and said density gradient of said layer of $Al_2O_3$ function to produce a linear response to relative humidity from said sensor.

6. A semiconductor for use as sensor for detecting relative humidity and temperature simultaneously *which does not exhibit progressive aging* comprising:
   a lower electrode formed from a noble metal;
   an essentially pure layer of $Al_2O_3$ having a thickness ranging from approximately 120 angstroms to 5000 angstroms deposited on said lower electrode, said layer of $Al_2O_3$ having a disordered crystalline structure *without pores* and a density gradient which varies progressively through the thickness of said layer of $Al_2O_3$ from a less dense structure at the lower surface of said layer of $Al_2O_3$ adjacent said lower electrode to a more dense structure at the upper surface of said layer of $Al_2O_3$;
   an upper electrode deposited on said upper surface of said layer of $Al_2O_3$, said upper electrode having a thickness ranging from approximately 7 Å to approximately 1000 Å;
   whereby said disordered crystalline structure and said density gradient of said layer of $Al_2O_3$ function to produce a linear response to relative humidity from said sensor and said upper electrode displays a change in resistance to changes in temperature when biased with a dc source.

Claims 2–5, dependent on an amended claim, are determined to be patentable.

* * * * *